(12) United States Patent
Vattikuti et al.

(10) Patent No.: US 10,966,971 B2
(45) Date of Patent: Apr. 6, 2021

(54) PHARMACEUTICAL COMPOSITIONS OF POMALIDOMIDE

(71) Applicant: Natco Pharma Limited, Hyderabad (IN)

(72) Inventors: Satyanarayana Vattikuti, Hyderabad (IN); Krishna Murthy Bhavanasi, Hyderabad (IN); Naveen Krishna Yalamanchalli, Hyderabad (IN); Venkaiah Chowdary Nannapaneni, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

(21) Appl. No.: 16/485,959

(22) PCT Filed: May 17, 2017

(86) PCT No.: PCT/IN2017/050182
§ 371 (c)(1),
(2) Date: Aug. 14, 2019

(87) PCT Pub. No.: WO2018/150435
PCT Pub. Date: Aug. 23, 2018

(65) Prior Publication Data
US 2020/0054621 A1 Feb. 20, 2020

(30) Foreign Application Priority Data

Feb. 18, 2017 (IN) .............................. 201741005805

(51) Int. Cl.
*A61K 31/454* (2006.01)
*A61K 9/48* (2006.01)

(52) U.S. Cl.
CPC .......... *A61K 31/454* (2013.01); *A61K 9/4858* (2013.01); *A61K 9/4866* (2013.01)

(58) Field of Classification Search
CPC ............................. A61K 31/454; A61K 9/4858
USPC ......................................................... 514/323
See application file for complete search history.

(56) References Cited

U.S. PATENT DOCUMENTS

| | | | |
|---|---|---|---|
| 5,635,517 | A | 6/1997 | Muller et al. |
| 8,828,427 | B2 | 9/2014 | Tutino et al. |
| 2014/0336223 | A1 | 11/2014 | Tutino et al. |
| 2016/0206607 | A1 | 7/2016 | Tutino et al. |
| 2016/0377621 | A1 | 12/2016 | Yarchoan et al. |

FOREIGN PATENT DOCUMENTS

| | | | | |
|---|---|---|---|---|
| CN | 104024590 A | 9/2014 | | |
| EP | 2391355 A2 | 12/2011 | | |
| WO | WO-2010135396 A2 * | 11/2010 | ............. | A61P 31/00 |
| WO | WO/2011/050962 A1 | 5/2011 | | |

* cited by examiner

*Primary Examiner* — Kevin E Weddington
(74) *Attorney, Agent, or Firm* — Vos-IP, LLC

(57) ABSTRACT

The invention relates to pharmaceutical compositions of pomalidomide comprising pomalidomide and binder or filler at amount of at most 89% weight percent of total weight of the composition and process for the preparation of such compositions.

3 Claims, No Drawings

PHARMACEUTICAL COMPOSITIONS OF POMALIDOMIDE

CROSS-REFERENCE TO RELATED APPLICATIONS

This application is a 371 of PCT Application No. PCT/IN2017/050182 filed on May 17, 2017, which claims the benefit of Indian Patent Application No. 201741005805 filed on Feb. 18, 2017, the contents of which are incorporated herein by reference in their entirety.

FIELD OF INVENTION

The invention relates to oral pharmaceutical compositions of pomalidomide and process for the preparation of such compositions.

BACKGROUND OF THE INVENTION

Pomalidomide, which is also known as CC-4047, is chemically named 4-amino-2-(2,6-dioxopiperidine-3-yl)isoindoline-1,3-dione. Pomalidomide is an immunomodulatory compound that inhibits, for example, LPS induced monocyte TNFα, IL-1β, IL-12, IL-6, MIP-1, MCP-1, GM-CSF, G-CSF, and COX-2 production. The compound is also known to costimulate the activation of T-cells. Pomalidomide and method of synthesizing the compound are described, e.g., in U.S. Pat. No. 5,635,517, the entirety of which is incorporated herein by reference.

Pomalidomide is commercially available as hard gelatin capsules for oral administration under the trade name POMALYST®. Pomalyst capsules contain 1 mg, 2 mg, 3 mg, or 4 mg of pomalidomide as active ingredient. Pomalyst is indicated for patients with multiple myeloma who have received at least two prior therapies including Lenalidomide and Bortezomib and have demonstrated disease progression on or within 60 days of completion of the last therapy. U.S. Pat. No. 8,828,427 and US Patent Publication Nos. US 2014-0336223 and US 2016-0206607 disclose capsule formulations of pomalidomide.

In the pharmaceutical industry, there is a constant need to work on identifying different pharmaceutical compositions that positively affect the drug's dissolution profile, bioavailability, bioequivalence, stability, etc., which all play important roles in determining a drug's market acceptance and success.

In the case of pomalidomide too, there is a need for the development of pharmaceutical compositions with improved solubility, stability, excellent storage, and handling stabilities, bioavailability, etc.

We herein after provide stable pharmaceutical compositions comprising pomalidomide and binder or filler at amount of at most 89% weight percent of total weight of the composition.

SUMMARY OF THE INVENTION

In one general aspect there is provided a pharmaceutical composition comprising pomalidomide and binder or filler at amount of at most 89% weight percent of total weight of the composition.

Embodiments of the present invention may include one or more of the following features for example the pharmaceutical composition may further include one or more pharmaceutical acceptable excipients. The pharmaceutical acceptable excipients may include diluents, disintegrants, surfactants, binders, lubricants, glidants, plasticizers, anti-foaming agents, antitacking agents, opacifying agents, and the like.

The details of one or more embodiments of the present invention are set forth in the description below. Other features, objects, and advantages of the invention will be apparent from the description.

DETAILED DESCRIPTION OF THE INVENTION

As used herein, the term "pomalidomide" is used in broad sense to include not only the pomalidomide per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs, and pharmaceutically acceptable prodrugs thereof, and also its various crystalline and amorphous forms.

The invention provides a pharmaceutical composition comprising: i) Pomalidomide and ii) binder or filler at an amount of at most 89% weight percent of total weight of the composition.

In an embodiment, the amount of pomalidomide in the pharmaceutical composition is from about 0.1 to 100 mg, preferably from about 0.5 to about 25 mg, more preferably from about 0.5 mg to 10 mg.

In another embodiment, the amount of filler or binder in the pharmaceutical composition is from about 1% to about 89%, preferably from about 40% to about 89%, more preferably from about 60% to about 89%, and most preferably from about 80% to about 89%.

In another embodiment, the binder or filler is starch, mannitol, or a mixture thereof In another embodiment, the starch is pregelatinized starch.

In another embodiment, the pharmaceutical composition is for oral administration.

In another embodiment, the pharmaceutical composition is in the form of capsules, caplets, tablets pellets, granules, solution, or suspension, preferably capsules.

In another embodiment, the process for the preparation of pharmaceutical compositions comprising pomalidomide comprising blending pomalidomide with at least one pharmaceutically acceptable excipient followed by filling the resultant blend into hard gelatin capsules.

In another embodiment, discloses a method for preventing and/or treating a cancer or related disease or disorder comprising administering the pomalidomide composition of the invention to a patient in need of such treatment.

Certain examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias.

The capsules contain from about 50 to 500 mg of the pharmaceutical composition (i.e., active ingredient and excipient[s]). Capsules can be of any size. Examples of standard sizes include #000, #00, #0, #1, #2, #3, #4, and #5.

Diluent includes, but are not limited to, powdered cellulose, microcrystalline cellulose, silicified microcrystalline cellulose, lactose, starch, dibasic calcium phosphate, tribasic calcium phosphate, calcium carbonate, dextrates, dextrin, dextrose, kaolin, magnesium carbonate, magnesium oxide, sugars such as sucrose; sugar alcohols such as mannitol, sorbitol, erythritol; and mixtures thereof.

Disintegrant includes, but are not limited to, croscarmellose sodium, sodium starch glycolate, pregelatinized starch, sodium carboxymethyl cellulose, microcrystalline cellulose, cross-linked polyvinylpyrrolidone, sodium alginate, and mixtures thereof.

Binder includes, but are not limited to, carrageenan, hydroxyethyl cellulose, hydroxypropyl cellulose, hydroxypropyl methylcellulose, carbomers, carboxymethylcellulose sodium, dextrin, ethyl cellulose, methylcellulose, shellac, zein, gelatin, polymethacrylates, polyvinyl pyrrolidone, pregelatinized starch, sodium alginate, gums, synthetic resins, and the like.

Lubricant includes, but are not limited to, metallic stearates such as magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, and mixtures thereof.

Capsules considered are soft gelatin, hard gelatin, HPMC, polysaccharide, or starch capsules as plugged, welded, or glued capsules, of different size, color, and water content. Preferably, hard gelatin capsules.

The invention is further illustrated by the following examples which are provided to be exemplary of the invention and do not limit the scope of the invention. While the present invention has been described in terms of its specific embodiments, certain modifications, and equivalents will be apparent to those skilled in the art and are intended to be included within the scope of the present invention.

EXAMPLES

TABLE 1

| S. No. | Ingredient | Quantity/Capsule (mg) | | | |
|---|---|---|---|---|---|
| | | Ex. 1 | Ex. 2 | Ex. 3 | Ex. 4 |
| 1 | Pomalidomide | 1.000 | 2.000 | 3.000 | 4.000 |
| 2 | Mannitol | 40.00 | 80.00 | 60.00 | 80.00 |
| 3 | Pregelatinized starch | 53.50 | 107.0 | 78.75 | 105.0 |
| 4 | Croscarmellose sodium | 15.00 | 30.00 | 22.50 | 30.00 |
| 5 | Sodium stearyl fumarate | 0.5 | 1.000 | 0.750 | 1.000 |

TABLE 1-continued

| S. No. | Ingredient | Quantity/Capsule (mg) | | | |
|---|---|---|---|---|---|
| | | Ex. 1 | Ex. 2 | Ex. 3 | Ex. 4 |
| | Net fill weight | 110.0 | 220.0 | 165.0 | 220.0 |
| | Capsule size | 4 | 2 | 2 | 2 |

Process:
1. Mixing pomalidomide and ingredients 2-5.
2. Filling the mixture of Step 1 into hard gelatin capsules.

The capsules thus prepared were tested for dissolution, assay, and impurity profile. The dissolution was carried out in a USP Type-II (paddle) apparatus having 900 ml 0.1 N HCl as a dissolution medium at 50 RPM. The results of the tests are shown below in Table 2.

TABLE 2

| Assay | 101.7% |
|---|---|
| Dissolution | 94.1% drug release in 30 min |
| Hydroxylamine impurity | ND |
| Any individual impurity (maximum) | 0.01% |
| Total impurities | 0.02% |

While the invention has been described in terms of its specific embodiments, certain modifications, and equivalents will be apparent to those skilled in the art and are intended to be included within the scope of the invention.

We claim:

1. A pharmaceutical composition in the form of a capsule comprising: i) Pomalidomide; ii) binder or filler at an amount of 80% to 89%, wherein the binder or filler is a mixture of mannitol and pregelatinized starch; iii) a disintegrant selected from croscarmellose sodium, sodium starch glycolate, and crosslinked polyvinylpyrrolidone; and iv) a lubricant selected from sodium stearyl fumarate, stearic acid, magnesium stearate, and talc.

2. The pharmaceutical composition according to claim 1, wherein the amount of pomalidomide is 0.5 mg to 10 mg.

3. The pharmaceutical composition according to claim 1, wherein the composition comprises:
  i) about 1 to 4 mg of Pomalidomide;
  ii) about 40 to 80 mg of mannitol and about 53.5 to 105 mg of pregelatinized starch;
  iii) about 15 to 30 mg of croscarmellose sodium; and
  iv) about 0.5 to 1 mg of sodium stearyl fumarate.

* * * * *